(12) United States Patent
Wang et al.

(10) Patent No.: US 8,202,528 B2
(45) Date of Patent: Jun. 19, 2012

(54) IMPLANTABLE MEDICAL DEVICES WITH ELASTOMERIC BLOCK COPOLYMER COATINGS

(75) Inventors: Yunbing Wang, Sunnyvale, CA (US); Daniel Castro, Santa Clara, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 873 days.

(21) Appl. No.: 11/810,627

(22) Filed: Jun. 5, 2007

(65) Prior Publication Data

US 2008/0306591 A1    Dec. 11, 2008

(51) Int. Cl.
*A61F 13/00*    (2006.01)
*A61F 2/00*    (2006.01)
*A61F 2/06*    (2006.01)

(52) U.S. Cl. ......... 424/422; 424/423; 424/426; 623/1.1; 623/1.42; 623/1.44; 623/1.46

(58) Field of Classification Search ........................ None
See application file for complete search history.

(56) References Cited

U.S. PATENT DOCUMENTS

| | | |
|---|---|---|
| 3,687,135 A | 8/1972 | Stroganov et al. |
| 3,839,743 A | 10/1974 | Schwarcz |
| 3,900,632 A | 8/1975 | Robinson |
| 4,104,410 A | 8/1978 | Malecki |
| 4,110,497 A | 8/1978 | Hoel |
| 4,321,711 A | 3/1982 | Mano |
| 4,346,028 A | 8/1982 | Griffith |
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |

(Continued)

FOREIGN PATENT DOCUMENTS

DE    44 07 079    9/1994

(Continued)

OTHER PUBLICATIONS

U.S. Appl. No. 10/317,435, filed Dec. 11, 2002, Hossainy et al.

(Continued)

*Primary Examiner* — Fereydoun G Sajjadi
*Assistant Examiner* — Casey Hagopian
(74) *Attorney, Agent, or Firm* — Squire Sanders (US) LLP (57) ABSTRACT

Implantable medical devices with elastomeric block copolymer coatings are disclosed.

13 Claims, 2 Drawing Sheets

U.S. PATENT DOCUMENTS

| | | | |
|---|---|---|---|
| 4,902,289 A | 2/1990 | Yannas |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,460,818 A * | 10/1995 | Park et al. ............ 426/415 |
| 5,464,650 A | 11/1995 | Berg et al. |
| 5,502,158 A | 3/1996 | Sinclair et al. |
| 5,514,379 A | 5/1996 | Weissleder et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,667,767 A | 9/1997 | Greff et al. |
| 5,667,796 A | 9/1997 | Otten |
| 5,670,558 A | 9/1997 | Onishi et al. |
| 5,693,085 A | 12/1997 | Buirge et al. |
| 5,700,286 A | 12/1997 | Tartaglia et al. |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,780,807 A | 7/1998 | Saunders |
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,897,955 A | 4/1999 | Drumheller |
| 5,906,759 A | 5/1999 | Richter |
| 5,914,182 A | 6/1999 | Drumheller |
| 5,916,870 A | 6/1999 | Lee et al. |
| 5,922,005 A | 7/1999 | Richter et al. |
| 5,942,209 A | 8/1999 | Leavitt et al. |
| 5,948,428 A | 9/1999 | Lee et al. |
| 5,954,744 A | 9/1999 | Phan et al. |
| 5,957,975 A | 9/1999 | Lafont et al. |
| 5,965,720 A | 10/1999 | Gryaznov et al. |
| 5,971,954 A | 10/1999 | Conway et al. |
| 5,976,182 A | 11/1999 | Cox |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,986,169 A | 11/1999 | Gjunter |
| 5,997,468 A | 12/1999 | Wolff et al. |
| 6,010,445 A | 1/2000 | Armini et al. |
| 6,015,541 A | 1/2000 | Greff et al. |
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |
| 6,066,156 A | 5/2000 | Yan |
| 6,071,266 A | 6/2000 | Kelley |
| 6,074,659 A | 6/2000 | Kunz et al. |
| 6,080,177 A | 6/2000 | Igaki et al. |
| 6,080,488 A | 6/2000 | Hostettler et al. |
| 6,083,258 A | 7/2000 | Yadav |
| 6,093,463 A | 7/2000 | Thakrar |

| | | | | | | |
|---|---|---|---|---|---|---|
| 6,096,070 | A | 8/2000 | Ragheb et al. | 6,645,243 | B2 | 11/2003 | Vallana et al. |
| 6,096,525 | A | 8/2000 | Patnaik | 6,656,162 | B2 | 12/2003 | Santini, Jr. et al. |
| 6,099,562 | A | 8/2000 | Ding et al. | 6,664,335 | B2 | 12/2003 | Krishnan |
| 6,103,230 | A | 8/2000 | Billiar et al. | 6,666,214 | B2 | 12/2003 | Canham |
| 6,107,416 | A | 8/2000 | Patnaik et al. | 6,667,049 | B2 | 12/2003 | Janas et al. |
| 6,110,188 | A | 8/2000 | Narciso, Jr. | 6,669,723 | B2 | 12/2003 | Killion et al. |
| 6,113,629 | A | 9/2000 | Ken | 6,676,697 | B1 | 1/2004 | Richter |
| 6,117,979 | A | 9/2000 | Hendriks et al. | 6,679,980 | B1 | 1/2004 | Andreacchi |
| 6,120,536 | A | 9/2000 | Ding et al. | 6,689,375 | B1 | 2/2004 | Wahlig et al. |
| 6,120,904 | A | 9/2000 | Hostettler et al. | 6,695,920 | B1 | 2/2004 | Pacetti et al. |
| 6,121,027 | A | 9/2000 | Clapper et al. | 6,706,273 | B1 | 3/2004 | Roessler |
| 6,125,523 | A | 10/2000 | Brown et al. | 6,709,379 | B1 | 3/2004 | Brandau et al. |
| 6,127,173 | A | 10/2000 | Eckstein et al. | 6,719,934 | B2 | 4/2004 | Stinson |
| 6,129,761 | A | 10/2000 | Hubbell | 6,719,989 | B1 | 4/2004 | Matsushima et al. |
| 6,129,928 | A | 10/2000 | Sarangapani et al. | 6,720,402 | B2 | 4/2004 | Langer et al. |
| 6,150,630 | A | 11/2000 | Perry et al. | 6,746,773 | B2 | 6/2004 | Llanos et al. |
| 6,153,252 | A | 11/2000 | Hossainy et al. | 6,752,826 | B2 | 6/2004 | Holloway et al. |
| 4,776,337 | A | 12/2000 | Palmaz | 6,753,007 | B2 | 6/2004 | Haggard et al. |
| 6,159,951 | A | 12/2000 | Karpeisky et al. | 6,764,505 | B1 | 7/2004 | Hossainy et al. |
| 6,160,084 | A | 12/2000 | Langer et al. | 6,818,063 | B1 | 11/2004 | Kerrigan |
| 6,165,212 | A | 12/2000 | Dereume et al. | 6,846,323 | B2 | 1/2005 | Yip et al. |
| 6,166,130 | A | 12/2000 | Rhee et al. | 7,166,099 | B2 | 1/2007 | Devens, Jr. |
| 6,169,170 | B1 | 1/2001 | Gryaznov et al. | 2001/0044652 | A1 | 11/2001 | Moore |
| 6,171,609 | B1 | 1/2001 | Kunz | 2002/0002399 | A1 | 1/2002 | Huxel et al. |
| 6,174,330 | B1 | 1/2001 | Stinson | 2002/0004060 | A1 | 1/2002 | Heublein et al. |
| 6,177,523 | B1 | 1/2001 | Reich et al. | 2002/0004101 | A1 | 1/2002 | Ding et al. |
| 6,183,505 | B1 | 2/2001 | Mohn, Jr. et al. | 2002/0062148 | A1 | 5/2002 | Hart |
| 6,187,045 | B1 | 2/2001 | Fehring et al. | 2002/0065553 | A1 | 5/2002 | Weber |
| 6,210,715 | B1 | 4/2001 | Starling et al. | 2002/0111590 | A1 | 8/2002 | Davila et al. |
| 6,224,626 | B1 | 5/2001 | Steinke | 2002/0116050 | A1 | 8/2002 | Kocur |
| 6,228,845 | B1 | 5/2001 | Donovan et al. | 2002/0138133 | A1 | 9/2002 | Lenz et al. |
| 6,240,616 | B1 | 6/2001 | Yan | 2002/0161114 | A1 | 10/2002 | Gunatillake et al. |
| 6,245,076 | B1 | 6/2001 | Yan | 2003/0033001 | A1 | 2/2003 | Igaki |
| 6,245,103 | B1 | 6/2001 | Stinson | 2003/0065355 | A1 | 4/2003 | Weber |
| 6,248,344 | B1 | 6/2001 | Ylanen et al. | 2003/0093107 | A1 | 5/2003 | Parsonage et al. |
| 6,251,135 | B1 | 6/2001 | Stinson et al. | 2003/0100865 | A1 | 5/2003 | Santini, Jr. et al. |
| 6,251,142 | B1 | 6/2001 | Bernacca et al. | 2003/0105518 | A1 | 6/2003 | Dutta |
| 6,273,913 | B1 | 8/2001 | Wright et al. | 2003/0105530 | A1 | 6/2003 | Pirhonen |
| 6,281,262 | B1 | 8/2001 | Shikinami | 2003/0120334 | A1* | 6/2003 | Gerberding ............... 623/1.15 |
| 6,284,333 | B1 | 9/2001 | Wang et al. | 2003/0171053 | A1 | 9/2003 | Sanders |
| 6,287,332 | B1 | 9/2001 | Bolz et al. | 2003/0187495 | A1 | 10/2003 | Cully et al. |
| 6,290,721 | B1 | 9/2001 | Heath | 2003/0208259 | A1 | 11/2003 | Penhasi |
| 6,293,966 | B1 | 9/2001 | Frantzen | 2003/0209835 | A1 | 11/2003 | Chun et al. |
| 6,303,901 | B1 | 10/2001 | Perry et al. | 2003/0226833 | A1 | 12/2003 | Shapovalov et al. |
| 6,312,459 | B1 | 11/2001 | Huang et al. | 2003/0236565 | A1 | 12/2003 | DiMatteo et al. |
| 6,327,772 | B1 | 12/2001 | Zadno-Azizi et al. | 2004/0093077 | A1 | 5/2004 | White et al. |
| 4,733,665 | C2 | 1/2002 | Palmaz | 2004/0098095 | A1 | 5/2004 | Burnside et al. |
| 6,375,826 | B1 | 4/2002 | Wang et al. | 2004/0111149 | A1 | 6/2004 | Stinson |
| 6,379,381 | B1 | 4/2002 | Hossainy et al. | 2004/0127970 | A1 | 7/2004 | Saunders et al. |
| 6,387,121 | B1 | 5/2002 | Alt | 2004/0143317 | A1 | 7/2004 | Stinson et al. |
| 6,388,043 | B1 | 5/2002 | Langer et al. | 2004/0167610 | A1 | 8/2004 | Fleming, III |
| 6,395,326 | B1 | 5/2002 | Castro et al. | 2005/0112170 | A1* | 5/2005 | Hossainy et al. ............ 424/423 |
| 6,409,761 | B1 | 6/2002 | Jang | 2005/0169968 | A1* | 8/2005 | Elmaleh et al. ............... 424/426 |
| 6,423,092 | B2 | 7/2002 | Datta et al. | 2006/0093771 | A1 | 5/2006 | Rypacek et al. |
| 6,461,632 | B1 | 10/2002 | Gogolewski | 2007/0282435 | A1* | 12/2007 | Wang et al. .................. 623/1.38 |
| 6,464,720 | B2 | 10/2002 | Boatman et al. | | | | |
| 6,479,565 | B1 | 11/2002 | Stanley | | | | |
| 6,485,512 | B1 | 11/2002 | Cheng | | | | |
| 6,492,615 | B1 | 12/2002 | Flanagan | | | | |
| 6,494,908 | B1 | 12/2002 | Huxel et al. | | | | |
| 6,495,156 | B2 | 12/2002 | Wenz et al. | | | | |
| 6,511,748 | B1 | 1/2003 | Barrows | | | | |
| 6,517,888 | B1 | 2/2003 | Weber | | | | |
| 6,527,801 | B1 | 3/2003 | Dutta | | | | |
| 6,537,589 | B1 | 3/2003 | Chae et al. | | | | |
| 6,539,607 | B1 | 4/2003 | Fehring et al. | | | | |
| 6,540,777 | B2 | 4/2003 | Stenzel | | | | |
| 6,554,854 | B1 | 4/2003 | Flanagan | | | | |
| 6,565,599 | B1 | 5/2003 | Hong et al. | | | | |
| 6,569,191 | B1 | 5/2003 | Hogan | | | | |
| 6,569,193 | B1 | 5/2003 | Cox et al. | | | | |
| 6,572,672 | B2 | 6/2003 | Yadav et al. | | | | |
| 6,574,851 | B1 | 6/2003 | Mirizzi | | | | |
| 6,585,755 | B2 | 7/2003 | Jackson et al. | | | | |
| 6,592,614 | B2 | 7/2003 | Lenker et al. | | | | |
| 6,592,617 | B2 | 7/2003 | Thompson | | | | |
| 6,613,072 | B2 | 9/2003 | Lau et al. | | | | |
| 6,626,939 | B1 | 9/2003 | Burnside et al. | | | | |
| 6,635,269 | B1 | 10/2003 | Jennissen | | | | |

FOREIGN PATENT DOCUMENTS

| | | |
|---|---|---|
| DE | 197 31 021 | 1/1999 |
| DE | 198 56 983 | 12/1999 |
| EP | 0 108 171 | 5/1984 |
| EP | 0 144 534 | 6/1985 |
| EP | 0281482 * | 3/1988 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 970 711 | 1/2000 |
| GB | 2 247 696 | 3/1992 |
| WO | WO 89/03232 | 4/1989 |
| WO | WO 90/01969 | 3/1990 |
| WO | WO 90/04982 | 5/1990 |
| WO | WO 90/06094 | 6/1990 |

| | | |
|---|---|---|
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 98/04415 | 2/1998 |
| WO | WO 99/03515 | 1/1999 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 2004/023985 | 3/2004 |
| WO | WO 2007/089435 | 8/2007 |
| WO | WO 2008/027107 | 3/2008 |
| WO | WO 2008/144418 | 11/2008 |

OTHER PUBLICATIONS

Acquarulo et al., *Enhancing Medical Device Performance with Nanocomposite Poly*, Med. Device Link, www.devicelink.com/grabber.php3?URL downloaded Mar. 26, 2007, 4 pgs.

Anonymous, *Bioabsorbable stent mounted on a catheter having optical coherence tomography capabilities*, Research Disclosure, Sep. 2004, pp. 1159-1162.

Ansari, *End-to-end tubal anastomosis using an absorbable stent*, Fertility and Sterility, vol. 32(2), pp. 197-201 (Aug. 1979).

Ansari, *Tubal Reanastomosis Using Absorbable Stent*, International Journal of Fertility, vol. 23(4), pp. 242-243 (1978).

Bull, *Parylene Coating for Medical Applications*, Medical Product Manufacturing News 18, 1 pg. (Mar. 1993).

Casper et al., *Fiber-Reinforced Absorbable Composite for Orthopedic Surgery*, Polymeric Materials Science and Engineering, vol. 53 pp. 497-501 (1985).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).

Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).

Devanathan et al., *Polymeric Conformal Coatings for Implantable Electronic Devices*, IEEE Transactions on Biomedical Engineering, vol. BME-27(11), pp. 671-675 (1980).

Elbert et al., *Conjugate Addition Reactions Combined with Free-Radical Cross-Linking for the Design of Materials for Tissue Engineering*, Biomacromolecules, vol. 2, pp. 430-441 (2001).

Hahn et al., *Biocompatibility of Glow-Discharge-Polymerized Films and Vacuum-Deposited Parylene*, J Applied Polymer Sci, vol. 38, pp. 55-64 (1984).

Hahn et al., *Glow Discharge Polymers as Coatings for Implanted Devices*, ISA, pp. 109-111 (1981).

He et al., *Assessment of Tissue Blood Flow Following Small Artery Welding with an Intraluminal Dissolvable Stent*, Microsurgery, vol. 19(3), pp. 148-152 (1999).

Kelley et al., *Totally Resorbable High-Strength Composite Material*, Advances in Biomedical Polymers, vol. 35, pp. 75-85 (1987).

Kubies et al., *Microdomain Structure in polylactide-block-poly(ethylene oxide) copolymer films*, Biomaterials, vol. 21, pp. 529-536 (2000).

Kutryk et al., *Coronary Stenting: Current Perspectives*, a companion to the Handbook of Coronary Stents, pp. 1-16 (1999).

Martin et al., *Enhancing the biological activity of immobilized osteopontin using a type-1 collagen affinity coating*, J. Biomed. Mater. Res., vol. 70A, pp. 10-19 (2004).

Mauduit et al., *Hydrolytic degradation of films prepared from blends of high and low molecular weight poly(DL-lactic acid)s*, J. Biomed. Mater. Res., vol. 30, pp. 201-207 (1996).

Middleton et al., *Synthetic biodegradable polymers as orthopedic devices*, Biomaterials, vol. 21, pp. 2335-2346 (2000).

Muller et al., *Advances in Coronary Angioplasty: Endovascular Stents*, Coron. Arter. Dis., vol. 1(4), pp. 438-448 (Jul./Aug. 1990).

nanoComposix, products, www.nanocomposix.com, downloaded Mar. 26, 2007, 2 pgs.

Nanosiliver, Photocatalyst and Nanocomposite Material, http://eng.nanocomposite.net downloaded Mar. 26, 2007, 1 pg.

Nichols et al., *Electrical Insulation of Implantable Devices by Composite Polymer Coatings*, ISA Transactions, vol. 26(4), pp. 15-18 (1987).

Peuster et al., *A novel approach to temporary stenting: degradable cardiovascular stents produced from corrodible metal-results 6-18 months after implantation into New Zealand white rabbits*, Heart, vol. 86, pp. 563-569 (2001).

Pietrzak et al., *Bioabsorbable Fixation Devices: Status for the Craniomaxillofacial Surgeon*, J. Craniofaxial Surg., vol. 2, pp. 92-96 (1997).

Pietrzak et al., *Bioresorbable implants—practical considerations*, Bone, vol. 19, No. 1, Supplement Jul. 1996, pp. 109S-119S.

Redman, *Clinical Experience with Vasovasostomy Utilizing Absorbable Intravasal Stent*, Urology, vol. 20(1), pp. 59-61 (Jul. 1982).

Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).

Schatz, *A View of Vascular Stents*, Circulation, vol. 79(2), pp. 445-457 (Feb. 1989).

Schmidt et al., *Long-Term Implants of Parylene-C Coated Microelectrodes*, Med & Biol Eng & Comp, vol. 26(1), pp. 96-101 (Jan. 1988).

Spagnuolo et al., *Gas 1 is induced by VE-cadherin and vascular endothelial growth factor and inhibits endothelial cell apoptosis*, Blood, vol. 103, pp. 3005-3012 (2004).

Tamai et al., *Initial and 6-Month Results of Biodegradable Poly-l-Lactic Acid Coronary Stents in Humans*, Circulation, pp. 399-404 (Jul. 25, 2000).

Tsuji et al., *Biodegradable Polymeric Stents*, Current Interventional Cardiology Reports, vol. 3, pp. 10-17 (2001).

Völkel et al., *Targeting of immunoliposomes to endothelial cells using a single—chain Fv fragment directed against human endoglin (CD105)*, Biochimica et Biophysica Acta 1663, pp. 158-166 (2004).

von Recum et al., *Degradation of polydispersed poly(L-lactic acid) to modulate lactic acid release*, Biomaterials, vol. 16, pp. 441-445 (1995).

Yau et al., Modern Size-Exclusion Liquid Chromatography, Wiley-Interscience Publication, IX-XV (1979).

International Search Report for PCT/US2008/064261, mailed Sep. 14, 2009, 7 pgs.

* cited by examiner

IMPLANTABLE MEDICAL DEVICES WITH ELASTOMERIC BLOCK COPOLYMER COATINGS

BACKGROUND OF THE INVENTION

1. Field of the Invention

This invention relates to coatings for implantable medical devices composed of block copolymers.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a constraining member such as a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil. In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug. Potential problems with therapeutic coatings for polymeric implantable medical devices, such as stents, include insufficient toughness, slow degradation rate, and poor adhesion.

SUMMARY OF THE INVENTION

Various embodiments of the present invention include an implantable medical device a coating above a polymer surface of the device, the coating comprising: a block copolymer including an elastic block and an anchor block, the elastic block being a random or alternating copolymer and having elastomeric behavior at physiological conditions, the anchor block being miscible with the surface polymer.

DETAILED DESCRIPTION OF THE INVENTION

Various embodiments of the present invention include an implantable medical device with a coating having an elastomeric block copolymer above a polymeric surface of the device. The polymeric surface may be a surface of a polymer coating disposed above a substrate that can be composed of metal, polymer, ceramic, or other suitable material. Alternatively, the polymeric surface may be a surface of a polymeric substrate. "Above" a surface is defined as higher than or over a surface measured along an axis normal to the surface, but not necessarily in contact with the surface.

Figure 1:
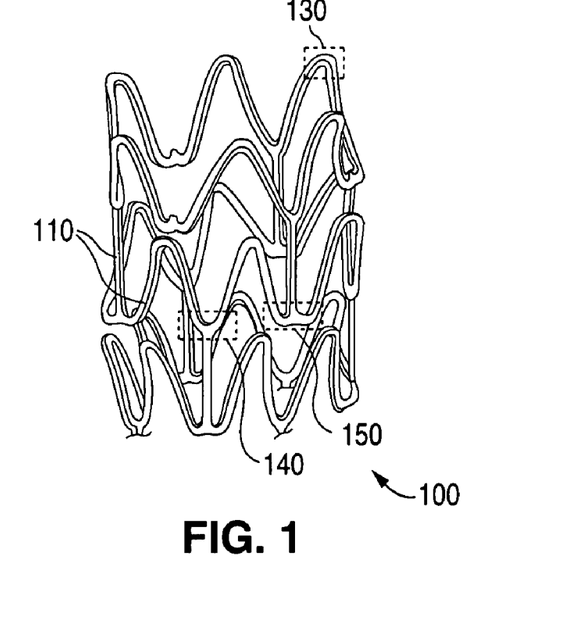
FIG. 1 depicts a view of a stent.

The present invention may be applied to implantable medical devices including, but not limited to, self-expandable stents, balloon-expandable stents, stent-grafts, and grafts (e.g., aortic grafts), and generally expandable tubular devices for various bodily lumen or orifices. A stent can have a scaffolding or a substrate that includes a pattern of a plurality of interconnecting structural elements or struts. FIG. 1 depicts a view of an exemplary stent 100. Stent 100 includes a pattern with a number of interconnecting structural elements or struts 110. In general, a stent pattern is designed so that the stent can be radially compressed (crimped) and radially expanded (to allow deployment). The stresses involved during compression and expansion are generally distributed throughout various structural elements of the stent pattern. The variations in stent patterns are virtually unlimited.

In some embodiments, a stent may be fabricated by laser cutting a pattern on a tube or a sheet rolled into a tube. Representative examples of lasers that may be used include, but are not limited to, excimer, carbon dioxide, and YAG. In other embodiments, chemical etching may be used to form a pattern on a tube.

An implantable medical device can be made partially or completely from a biodegradable, bioabsorbable, biostable polymer, or a combination thereof. A polymer for use in fabricating an implantable medical device can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes.

As indicated above, a medicated implantable medical device, such as a stent, may be fabricated by coating the surface of a stent with a drug. For example, a device can have a coating including a drug dispersed in a polymeric carrier disposed over a substrate of the stent. Such a coating layer may be formed by applying a coating material to a substrate of an implantable medical device, such as a stent. The coating material can be a polymer solution and a drug dispersed in the solution. The coating material may be applied to the stent by immersing the stent in the coating material, by spraying the material onto the stent, or by other methods known in the art. The solvent in the solution is then removed, for example, by evaporation, leaving on the stent surfaces a polymer coating impregnated with the drug.

Stents are typically subjected to stress during use. "Use" includes manufacturing, assembling (e.g., crimping a stent on balloon), delivery of a stent through a bodily lumen to a treatment site, deployment of a stent at a treatment site, and treatment after deployment. Both the underlying scaffolding or substrate and the coating experience stress that result in strain in the substrate and coating. In particular, localized portions of the stent's structure undergo substantial deformation. For example, the apex regions of bending elements 130, 140, and 150 in FIG. 1 experience relatively high stress and strain during crimping, expansion, and after expansion of the stent.

Furthermore, polymer substrates and polymer-based coatings may be particularly vulnerable to mechanical instability during use of a stent. Such mechanical instability for coatings can include fracture and detachment from a substrate, for exampling, peeling. Some polymers may be susceptible to such mechanical instability due to insufficient toughness at high deformations. Additionally, detachment of coatings may be due to poor adhesion of the polymer-based coating to the substrate or another polymer layer. Therefore, polymer-based coatings are highly susceptible to tearing or fracture, and/or detachment, especially at regions subjected to relatively high stress and strain. Thus, it is important for a polymer-based coating to (1) be tough and have a high resistance to cracking and (2) have good adhesion with an underlying layer or substrate and to have a high resistance to detachment in the range of deformations that occur during crimping, during deployment of a stent, and after deployment.

As indicated above, a device may be composed in whole or in part of materials that degrade, erode, or disintegrate through exposure to physiological conditions within the body until the treatment regimen is completed. The device may be configured to disintegrate and disappear from the region of implantation once treatment is completed. The device may disintegrate by one or more mechanisms including, but not limited to, dissolution and chemical breakdown. The duration of a treatment period depends on the bodily disorder that is being treated. For illustrative purposes only, in treatment of coronary heart disease involving use of stents in diseased vessels, the duration can be in a range from about a month to a few years. However, the duration is typically in a range from about six to twelve months. Thus, it is desirable for polymer-based coatings and substrates of an implantable medical device, such as a stent, to have a degradation time at or near the duration of treatment. Degradation time refers to the time for an implantable medical device to substantially or completely erode away from an implant site.

Embodiments of the present invention include an implantable medical device including a coating above a polymer surface of the device, the coating including a block copolymer including an elastic block and an anchor block. The elastic block exhibits elastomeric or rubbery behavior at physiological conditions. In some embodiments, the elastic block, the anchor block, or both can be bioabsorable polymers. In addition, the anchor block is miscible with the surface polymer. In some embodiments, all or a majority of the coating may be the block copolymer. Additionally, the coating can be a therapeutic layer with an active agent or drug mixed or dispersed within the block copolymer.

In such embodiments, the block copolymer can have more than one elastic block and more than one anchor block. In one embodiment, the block copolymer can have an elastic block on one end and an anchor block at another end. In another embodiment, the block copolymer can have an elastic block between two anchor blocks or anchor block between two elastic blocks.

Figure 2A:
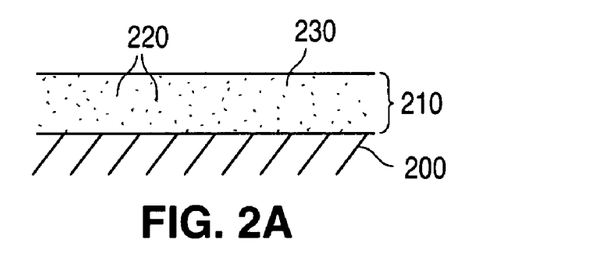
FIG. 2A depicts a cross-section of a stent surface with a block copolymer coating layer over a substrate.

In certain embodiments, the block copolymer coating is disposed directly over the surface of a polymer substrate of a device, such as a stent scaffolding. FIG. 2A depicts a cross-section of a stent surface with a block copolymer coating layer 210 over a substrate 200. In the embodiment shown in FIG. 2A, block-copolymer coating layer 210 includes a drug 220 dispersed in a block copolymer 230. The substrate can be composed of a bioabsorbable polymer.

Figure 2B:
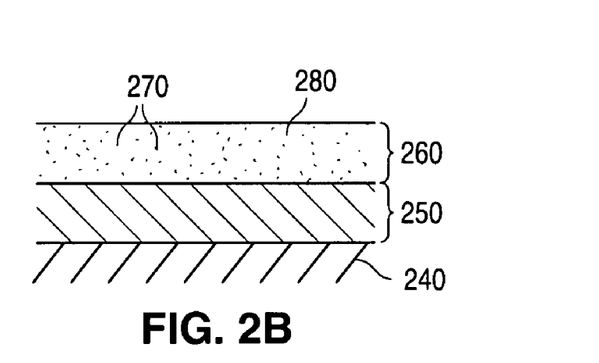
FIG. 2B depicts a cross-section of a stent surface with a block copolymer coating layer over a polymeric layer disposed over a substrate of the stent.

In other embodiments, the block copolymer coating can be over a polymer coating layer that is disposed over a substrate. FIG. 2B depicts a cross-section of a substrate 240 of a stent with a polymeric layer 250 disposed over substrate 240. A block copolymer coating layer 260 is disposed over polymeric layer 250. Coating layer 260 includes a drug 270 dispersed within a block copolymer 280. Polymeric layer 250 can be a primer layer for improving the adhesion of drug-polymer layer 260 to substrate 240. In the embodiment of FIG. 2B, substrate 240 can be metallic, polymeric, ceramic, or other suitable material.

In some embodiments, the block copolymer coating exhibits a rubbery or elastomeric behavior at physiological conditions. An "elastomeric" or "rubbery" polymer refers to a polymer that exhibits elastic deformation through all or most of a range of deformation. Physiological conditions include, but are not limited to, human body temperature, approximately 37° C. The elastic block of the block copolymer is an elastomeric or rubbery polymer that allows or provides the elastomeric or rubbery properties of the coating. Such elastomeric properties provide the coating with a high fracture toughness during use of a device such as a stent. In some embodiments, the elastic blocks can have glass transition temperature (Tg) below body temperature. Additionally, the block copolymer may be completely or substantially amorphous.

In some embodiments, the elastic block of the block copolymer includes functional groups or units that provide the rubbery or elastic properties to the block copolymer. In such embodiments, the elastic block can be a random or alternating copolymer that includes units, referred to herein as "elastic units," that form elastic or rubbery polymers at physiological conditions. Biodegradable polymers that are elastomer or rubber at physiological conditions include, but are not limited to, polycaprolactone (PCL), poly(tetramethyl carbonate) (PTMC), poly(4-hydroxy butyrate) (PHB), and polydioxanone (PDO). Some embodiments of the elastic blocks of the block copolymer can include caprolactone (CL), tetramethyl carbonate (TMC), 4-hydroxy butyrate (HB), dioxanone (DO), or a combination thereof. Exemplary elastic blocks can include at least two types of functional units, for example, P(CL-co-TMC), P(CL-co-HB), P(CL-DO), etc.

In additional embodiments, the elastic block can be a copolymer of at least one elastic unit and an additional unit. A homopolymer of the additional unit may be a glassy polymer with a Tg above body temperature. The additional unit may be selected so that it increases the degradation rate of the copolymer. For example, the additional "fast eroding" units may be more hydrophilic or more hydrolytically active than the elastic unit. Additionally, the additional unit may have acidic and hydrophilic degradation products. Since the rate of the hydrolysis reaction tends to increase as the pH decreases, acidic degradation products can increase the degradation rate of the block copolymer. Glycolide (GA) units, for example, have acidic degradation products which can increase the degradation rate of the coating. Exemplary elastic blocks can include P(CL-co-GA), P(GA-co-TMC), P(GA-DO), etc.

In some embodiments, the toughness and degradation rate of the block copolymer coating can be adjusted by the ratio of elastic and non-elastic units. As the ratio of CL, for example, increases in P(GA-co-CL) segments, the block copolymer becomes more flexible and tougher. The Tg of the elastic block can be tuned to a desired value by adjusting the ratio of component monomers. Additionally, the degradation rate of the block copolymer coating can be increased by increasing the fraction of "fast eroding units," such as GA, in the elastic blocks. In exemplary embodiments, the P(GA-co-CL) segments can have up to 1 wt %, 5 wt %, 20 wt %, or 50 wt % GA units.

As discussed above, the anchor block of the block copolymer can be miscible with the surface polymer. In one embodiment, the anchor block can have the same chemical composition as the surface polymer. Alternatively, the anchor block can have a chemical composition different from the surface polymer, but similar enough so that the anchor block is miscible with the surface polymer. In an exemplary embodiment, the block copolymer can have a PLLA anchor block and be disposed over a PLLA surface, which can be the surface of a PLLA substrate.

In certain embodiments, the anchor block can be a copolymer. In such embodiments, the composition of the anchor blocks of the block copolymer coating can be selected so that the anchor block is miscible with the surface polymer. In addition, the units of the copolymer can be selected to adjust the degradation rate of the block copolymer. In one embodiment, the anchor block can include units that are more hydrolytically active or hydrophilic than other units to increase the degradation rate of the coating. In an exemplary embodiment, the anchor block can be poly(L-lactide-co-glycolide) (LPLG). In such an embodiment, the surface polymer can be LPLG. The composition of LLA and GA in the anchor block can be adjusted so that the LPLG anchor block is miscible with the LPLG surface polymer. In some embodiments, the surface polymer can be a copolymer having a high percentage of LLA units, for example, at least 60 wt %, 70 wt %, or 80 wt % LLA units.

In further embodiments, the block copolymer coating can be applied to a polymer surface so that at least some of the elastomeric block copolymer is mixed within the surface polymer. In particular, at least the anchor blocks can be mixed within the surface polymer. It is believed that an interfacial region between the coating and the surface polymer can have block copolymer mixed with surface polymer. The anchor blocks of the block copolymer act as a compatibilizer that strengthens the bond between the coating and the coated surface. The interfacial region can enhance the adhesion of the block copolymer coating to the polymer substrate or polymer surface layer, in general.

Figure 3:
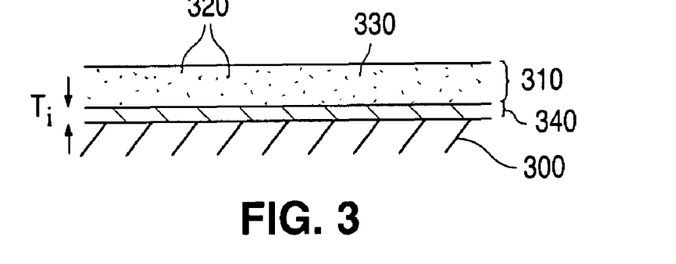
FIG. 3 depicts a cross-section of a stent surface with the block-copolymer coating layer over a substrate of the stent showing an interfacial region.

FIG. 3 depicts a cross-section of a stent surface with a block copolymer coating layer 310 over a substrate 300. Coating layer 310 can be applied to form an interfacial region 340 which can include anchor blocks mixed with substrate polymer. A drug 320 can be mixed or dispersed within coating layer 310 and interfacial region 340. A thickness Ti of interfacial region 340 can be varied depending on coating application processing parameters.

The enhanced adhesion can allow the use of a tough, high fracture resistant coating that may otherwise have poor adhesion to a polymer substrate of a device. The polymer material for a substrate of a device, such as a stent, may be selected primarily on the basis of strength and stiffness so that the stent substrate can provide support for a lumen. Such substrate polymers tend to be crystalline or semi-crystalline polymers that are glassy or have a Tg above body temperature. Tough, elastomeric polymers may not necessarily have good adhesion with such a substrate. Embodiments of the block copolymer with an anchor block allow the use of a tough, high fracture resistant coating over a glassy substrate. Such glassy substrate polymers include PLLA and LPLG.

Exemplary elastomeric block copolymers include, but are not limited to, P(CA-co-TMC)-b-PLLA, P(CA-co-TMC)-b-LPLG, P(CA-co-GA)-b-PLLA, P(CA-co-GA)-b-LPLG, P(TMC-co-GA)-b-PLLA, P(TMC-co-GA)-b-LPLG.

In exemplary embodiments, the molecular weight of the elastic blocks can be between 20 kg/mol and 150 kg/mol, or greater than 150 kg/mol. In exemplary embodiments, the molecular weight of the anchor blocks can be between 20 kg/mol_and 150 kg/mol, or greater than 150 kg/mol. The relative weight percent of the elastic blocks and the anchor blocks can be between 1:5 and 5:1.

In some embodiments, the block copolymer coating can include a dispersed polymer phase. In such embodiments, the anchor block can have a high enough molecular weight that a dispersed anchor block phase is formed within an elastomeric phase composed of the elastic blocks. In these embodiments, the anchor block can be a crystalline or semicrystalline polymer. The dispersed phase can be crystalline or semi-crystalline polymer regions that are dispersed within an amorphous elastomeric phase. The crystalline regions can be used to modify the delivery rate of a dispersed drug from the coating. The crystalline regions tend to increase the delivery rate of drug from the coating.

Embodiments of the elastomeric block copolymers disclosed herein can be formed by solution-based polymerization. Other methods of forming the block copolymers are also possible, such as, without limitation, melt phase polymerization.

Some embodiments of the solution polymerization involve forming the elastic blocks first and then the anchor blocks. In such embodiments, a solution is prepared including the elastic units for the elastic blocks, an appropriate solvent, an appropriate initiator, and catalyst in which the elastic blocks are formed from the monomers. The anchor block units for the anchor block and catalyst are then added to the solution to form anchor blocks that are bonded to the elastic blocks. The elastomeric block copolymer can be removed from the solution through precipitation in a non-solvent of the elastomeric block copolymer. The solvent(s) for the reaction mixture can be selected so that the elastic blocks formed are soluble in the solvent(s) to allow the elastic blocks to copolymerize with anchor blocks in solution.

For example, to prepare P(GA-co-CL)-b-PLLA block copolymer, P(GA-co-CL) elastic blocks are formed in a solution containing GA and CL monomers, a dodecanol initiator, and stannous octoate catalyst in a xylene solvent. L-lactide monomers can then be added to the solution. The L-lactide monomers react with P(GA-co-CL) to form P(GA-co-CL)-b-PLLA. The solution can then be added to methanol, which is a non-solvent for the formed block copolymer, to precipitate the elastomeric block copolymer from solution.

In other embodiments of solution polymerization, elastomeric block copolymers can be formed by reacting elastic blocks swollen with a solvent that contains anchor block monomers. The elastic blocks are swollen by a solvent after they are formed so that they can react with anchor block monomers. One of skill in the art can select a solvent that swells but does not dissolve the elastic blocks.

In one embodiment, the solvent for use in synthesizing the elastomeric block copolymer is devoid of alcohol functional groups. Such alcohol groups may act as initiators for chain growth in the polymer. Solvents used to synthesize the elastomeric block copolymer include, but are not limited to, chloroform, toluene, xylene, and cyclohexane.

Other embodiments of the solution polymerization involve forming the anchor blocks first and then the elastic blocks.

The block copolymer coating may be formed over an implantable medical device, such as a stent, by applying a coating material to a polymer surface of the device. The coating material can be a solution including the block copolymer. The solution can further include an active agent or drug dissolved in a solvent. As discussed above, the coating material may be applied to the stent by immersing the device in the coating material, by spraying the composition onto the device, or by other methods known in the art. The solvent in the solution is removed, leaving on the device surfaces the elastomeric block polymer coating and optionally drug dispersed within the polymer.

Drying or solvent removal can be performed by allowing the solvent to evaporate at room or ambient temperature. Depending on the volatility of the particular solvent employed, the solvent can evaporate essentially upon contact with the stent. Alternatively, the solvent can be removed by subjecting the coated stent to various drying processes. Drying time can be decreased to increase manufacturing throughput by heating the coated stent. For example, removal of the solvent can be induced by baking the stent in an oven at a mild temperature (e.g., 50° C.) for a suitable duration of time (e.g., 2-4 hours) or by the application of warm air. In an embodiment, a substantial portion of solvent removed may correspond to less than 5%, 3%, or more narrowly, less than 1% of solvent remaining after drying. Depositing a coating of a desired thickness in a single coating stage can result in an undesirably nonuniform surface structure and/or coating defects. Therefore, a coating process can involve multiple repetitions of application, for example, by spraying a plurality of layers.

In some embodiments, the solvent of the coating material is also a solvent for the surface polymer on which the coating material is applied. Specifically, a "solvent" for a given polymer can be defined as a substance capable of dissolving or dispersing the polymer or capable of at least partially dissolving or dispersing the polymer to form a uniformly dispersed mixture at the molecular- or ionic-size level. The solvent should be capable of dissolving at least 0.1 mg of the polymer in 1 ml of the solvent, and more narrowly 0.5 mg in 1 ml at ambient temperature and ambient pressure. The solvent in the coating material can dissolve at least a portion of the surface polymer upon application of the coating material to the polymer surface.

Due to dissolution of a portion of the surface polymer, the coating material near the surface of the surface polymer includes dissolved surface polymer in addition to the elastic block copolymer from the coating material. It is believed that upon removal of the solvent, an interfacial region, as depicted in FIG. 3, is formed that includes anchor blocks of the elastomeric block copolymer mixed with surface polymer. This interfacial region can be formed due to the miscibility of the surface polymer with the anchor blocks.

In other embodiments, the solvent in the coating material can be capable of swelling the surface polymer, but is incapable or substantially incapable of dissolving the surface polymer. A solvent that is capable of swelling the surface polymer and is incapable or substantially incapable of dissolving the polymer is understood to mean a sample of the surface polymer swells when immersed in the solvent and the swollen sample of the surface polymer remains in the solvent with a negligible loss of mass for an indefinite period of time at conditions of ambient temperature and pressure.

Solvents for polymers can be found in standard texts (e.g., see Fuchs, in Polymer Handbook, 3rd Edition and Deasy, Microencapsulation and Related Drug Processes, 1984, Marcel Dekker, Inc., New York.) The ability of a polymer to swell and to dissolve in a solvent can be estimated using the Cohesive Energy Density Concept (CED) and related solubility parameter values as discussed by Deasy and can be found in detail in the article by Grulke in Polymer Handbook.

Figure 4:
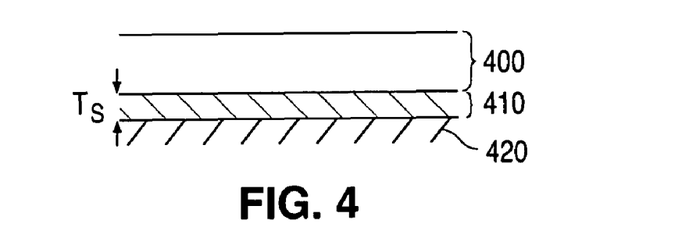
FIG. 4 depicts a cross-section of a stent showing a coating material layer over a swollen surface polymer layer.

FIG. 4 depicts a cross-section of a stent showing a coating material layer 400 over a swollen surface polymer layer 410. Swollen surface polymer layer 410 is over unswollen polymer coating layer or polymer substrate 420. As indicated above, unswollen surface polymer 420 can either be a substrate of the stent or a polymeric coating over a stent substrate. As shown, swollen surface polymer layer 410 has a thickness Ts. Due to swelling of the surface polymer in swollen polymer layer 410, it is believed that anchor blocks of the elastomeric block copolymer in coating material layer 400 penetrate into or mix with the surface polymer in swollen polymer layer 410 prior to removal of the solvent. Upon removal of the solvent, a coating layer is formed over substrate 420.

Figure 5:
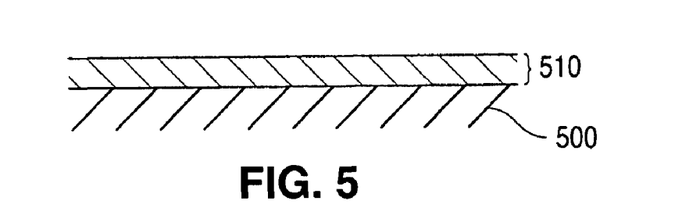
FIG. 5 depicts a polymer surface pretreated with a solvent.

In some embodiments, a polymeric substrate or polymeric surface coating layer can be pretreated with a solvent that dissolves or swells the surface polymer prior to applying a coating material. FIG. 5 depicts a layer 510 over a substrate or coating layer 500. Layer 510 can be a dissolved layer of surface polymer or a swollen layer of surface polymer. Following pretreatment, the coating material can be applied over the pretreated surface.

In certain embodiments, the coating material solvent is different from the pretreatment solvent. The use of a different solvent for the coating material and the pretreating can provide a degree of flexibility to the coating process. Generally, a treatment with a medicated stent may require a particular drug coating on a coating of a medicated stent. A drug may have an undesirably low or negligible solubility in a selected group of solvents that can dissolve or swell the surface polymer. Thus, a drug coating formed using such a solvent can have an undesirably low concentration of drug. A suitable pretreatment solvent can be used to dissolve or swell the surface polymer and a different solvent can be used as a coating solvent, in which the drug has an acceptable solubility. In general, a required solubility of a drug in a coating solvent is determined by the drug loading required of a particular treatment regimen. Specifically, it is desirable for a drug to have solubility of at least 1 wt % in a solvent for use as a coating material solvent for forming a drug-polymer layer on a stent.

Figure 6:
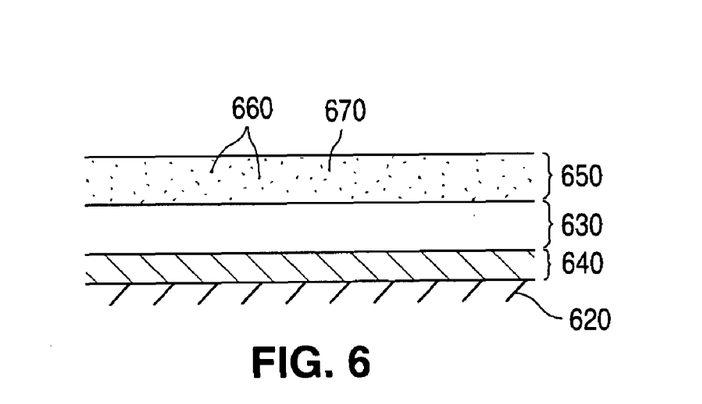
FIG. 6 depicts the cross-section of a stent surface with a drug-polymer layer over a block copolymer primer layer disposed over a substrate of the stent.

In other embodiments, an elastomeric block copolymer coating can be a primer layer over a polymer substrate or coating layer. The elastomeric block copolymer coating can act as a primer layer for a drug-polymer coating layer over the primer layer. The elastomeric block copolymer primer layer may be formed above a polymeric surface, as described above. The primer coating material can include an elastic block copolymer dissolved in a solvent that can dissolve or swell the surface polymer. A drug-polymer layer can then be formed over the elastomeric block copolymer primer layer. The drug coating material may include a polymer that is different from the elastomeric block copolymer and a solvent that is different from the primer coating material solvent. FIG. 6 depicts a drug layer 650 over primer coating layer 630. Drug layer 650 includes a drug 660 mixed or dispersed within a polymer 670. An interfacial layer 640, discussed above, includes anchor blocks and surface polymer.

In general, representative examples of polymers that may be used to fabricated a substrate of and coatings for an implantable device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(L-lactide-co-glycolide); poly(D,L-lactide), poly(caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially well suited for use in embodiments of the present invention include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

For the purposes of the present invention, the following terms and definitions apply:

For the purposes of the present invention, the following terms and definitions apply:

The "glass transition temperature," Tg, is the temperature at which the amorphous domains of a polymer change from a brittle vitreous state to a solid deformable, ductile, or rubbery state at atmospheric pressure. In other words, the Tg corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition.

"Stress" refers to force per unit area, as in the force acting through a small area within a plane. Stress can be divided into components, normal and parallel to the plane, called normal stress and shear stress, respectively. True stress denotes the stress where force and area are measured at the same time. Conventional stress, as applied to tension and compression tests, is force divided by the original gauge length.

"Strength" refers to the maximum stress along an axis which a material will withstand prior to fracture. The ultimate strength is calculated from the maximum load applied during the test divided by the original cross-sectional area.

"Strain" refers to the amount of elongation or compression that occurs in a material at a given stress or load.

"Elongation" may be defined as the increase in length in a material which occurs when subjected to stress. It is typically expressed as a percentage of the original length.

"Toughness" is the amount of energy absorbed prior to fracture, or equivalently, the amount of work required to fracture a material. One measure of toughness is the area under a stress-strain curve from zero strain to the strain at fracture. Thus, a brittle material tends to have a relatively low toughness.

Drugs or therapeutic active agent(s) can include anti-inflammatories, antiproliferatives, and other bioactive agents.

An antiproliferative agent can be a natural proteineous agent such as a cytotoxin or a synthetic molecule. Preferably, the active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin $I_1$, actinomycin $X_1$, and actinomycin $C_1$), all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy]ethyl-rapainycin, or 40-O-tetrazole-rapamycin, 40-epi-(N1-tetrazolyl)-rapamycin (ABT-578 manufactured by Abbott Laboratories, Abbott Park, Ill.), prodrugs thereof, co-drugs thereof, and combinations thereof. In one embodiment, the anti-proliferative agent is everolimus.

An anti-inflammatory drug can be a steroidal anti-inflammatory agent, a nonsteroidal anti-inflammatory agent, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazalen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptalnate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. In one embodiment, the anti-inflammatory agent is clobetasol.

Alternatively, the anti-inflammatory may be a biological inhibitor of proinflammatory signaling molecules. Anti-inflammatory biological agents include antibodies to such biological inflammatory signaling molecules.

In addition, drugs or active can be other than antiproliferative agents or anti-inflammatory agents. These active agents can be any agent which is a therapeutic, prophylactic, or a diagnostic agent. In some embodiments, such agents may be used in combination with antiproliferative or anti-inflammatory agents. These agents can also have anti-proliferative and/or anti-inflammatory properties or can have other properties such as antineoplastic, antiplatelet, anti-coagulant, anti-fibrin, antithrombonic, antimitotic, antibiotic, antiallergic, antioxidant, and cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues dextran, D-phe-pro-arg-chloromethylketone (synthetic antithrombin), dipyridamole, glycoprotein Ib/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, and genetically engineered epithelial cells. The foregoing substances are listed by way of example and are not meant to be limiting.

Other bioactive agents may include antiinfectives such as antiviral agents; analgesics and analgesic combinations; anorexics; antihelmintics; antiarthritics; antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives;

diuretics; vasodilators including general coronary; peripheral and cerebral; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents. Other active agents which are currently available or that may be developed in the future are equally applicable.

EXAMPLES

The examples set forth below are for illustrative purposes only and are in no way meant to limit the invention. The following examples are given to aid in understanding the invention, but it is to be understood that the invention is not limited to the particular materials or procedures of examples.

Example 1

P(GA-co-CL)-b-PLLA Copolymer Synthesis

In this example, 5 g glycolide (GA), 15 g caprolactone (CL), and 5 g L-lactide (LLA) as monomers, 0.056 mL stannous octoate as catalyst, 0.15 mL dodecanol as initiator and 50 ml xylene as solvent are used.

Step 1: One 500 mL reaction kettle with a mechanical stirring rod is placed in a glove box which is filled with high purity nitrogen. The reaction kettle is preheated to remove all moisture.

Step 2: GA, CL, dodecanol, xylene, and stannous octoate are added into the reaction kettle. The mixture is stirred at 120° C. for 72 hours.

Step 3: LLA is then added into reaction kettle and the reaction lasts for another 72 hours.

Step 4: 100 mL $CHCl_3$ is then added into reaction kettle to dilute final product. The product solution is precipitated into 600 mL methanol, filtered out, and dried in vacuum at 80° C. until constant weight.

Example 2

PLLA-b-P(GA-co-CL)-b-PLLA Copolymer Synthesis

In this example, 5 g glycolide (GA), 15 g caprolactone (CL), and 5 g L-lactide (LLA) as monomers, 0.056 mL stannous octoate as catalyst, 0.05 mL ethylene glycol as initiator and 50 ml xylene as solvent are used.

Step 1: One 500 mL reaction kettle with a mechanical stirring rod is placed in a glove box which is filled with high purity nitrogen. The reaction kettle is preheated to remove all moisture.

Step 2: GA, CL, ethylene glycol, xylene, and stannous octoate are added into the reaction kettle. The mixture is stirred at 120° C. for 72 hours.

Step 3: LLA is then added into reaction kettle and the reaction lasts for another 72 hours.

Step 4: 100 mL $CHCl_3$ is added into reaction kettle to dilute final product. The product solution is precipitated into 600 mL methanol, filtered out and dried in vacuum at 80° C. until constant weight.

Example 3

Preparation of Coating Solution and Coating Layer on PLLA Stent Backbone

The coating solution is prepared by mixing copolymer with drug in a solvent. The copolymer can be P(GA-co-CL)-b-PLLA, P(GA-co-TMC)-b-PLLA, PLLA-b-P(GA-co-CL)-b-PLLA, or PLLA-b-P(GA-co-TMC)-b-PLLA. Everolimus, Sirolimus, Paclitaxel, or their derivatives could be used as drug, and acetone, dimethylene chloroform, or their mixtures could be used as solvent. The weight ratio of copolymer to drug is in the range of 0.1:1 to 10:1, and the weight percent of copolymer in the solution is in the range of 0.1-4 wt %. The coating layer is prepared through spray/dip/drop coating of solution on stent backbone.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. An implantable medical device comprising a coating above a polymer surface of the device, the coating comprising:
   a block copolymer including an elastic block and an anchor block, the elastic block being a random or alternating copolymer and having elastomeric behavior at physiological conditions, the anchor block being miscible with the surface polymer, wherein the surface polymer and the anchor block comprise PLLA or LPLG and wherein the block copolymer is selected from the group consisting of P(GA-co-CL)-b-PLLA, P(GA-co-CL)-b-LPLG, P(GA-co-TMC)-b-PLLA, and P(GA-co-TMC)-b-LPLG.

2. The device of claim 1, wherein the device is a stent.

3. The device of claim 1, wherein the block copolymer is bioabsorbable.

4. The device of claim 1, wherein a body of the device is formed from a bioabsorbable polymer.

5. The device of claim 1, wherein a majority of the coating comprises the block copolymer.

6. The device of claim 1, wherein the polymer surface comprises a surface of the substrate of the device.

7. The device of claim 1, wherein the polymer surface comprises a surface of a coating layer above a substrate of the device.

8. The device of claim 1, wherein the coating comprises an active agent.

9. The device of claim 1, wherein the elastic block, anchor block, and the surface polymer are biodegradable, wherein the elastic block is faster degrading than the anchor block and the surface polymer.

10. The device of claim 1, wherein the anchor block is of the same chemical composition as the surface polymer.

11. The device of claim 1, wherein the elastic block has a Tg below body temperature, and wherein the anchor block and the surface polymer have a Tg above body temperature.

12. The device of claim 1, wherein coating comprises an interfacial region between the surface polymer and the coating in which anchor blocks are mixed with the surface polymer.

13. The device of claim 1, wherein anchor blocks enhance adhesion of the coating to the polymer surface.

* * * * *